(12) United States Patent
    Son (10) Patent No.: US 9,508,496 B2
(45) Date of Patent: Nov. 29, 2016

(54) AUTOMATIC SALT METER HAVING INTERNAL SWITCHING DEVICE

(71) Applicant: Yun-Ho Son, Seoul (KR)

(72) Inventor: Yun-Ho Son, Seoul (KR)

( * ) Notice: Subject to any disclaimer, the term of this patent is extended or adjusted under 35 U.S.C. 154(b) by 435 days.

(21) Appl. No.: 13/759,626

(22) Filed: Feb. 5, 2013

(65) Prior Publication Data

US 2013/0205876 A1     Aug. 15, 2013

(30) Foreign Application Priority Data

Feb. 10, 2012   (KR) .................... 10-2012-0013932
Jan. 4, 2013    (KR) .................... 10-2013-0000958

(51) Int. Cl.
    *G01N 33/02*    (2006.01)
    *H01H 9/04*     (2006.01)
    *H01H 3/60*     (2006.01)

(52) U.S. Cl.
    CPC ............... *H01H 9/04* (2013.01); *G01N 33/02* (2013.01); *H01H 3/60* (2013.01); *H01H 2009/048* (2013.01)

(58) Field of Classification Search
    CPC .............. H01H 35/027; H01H 35/14; H01H 9/04; H01H 3/60; H01H 2009/048; H01H 35/141; H01H 35/142; H01H 35/143; H01H 35/145; H01H 35/02; H01H 35/025; G01N 33/02
    USPC ....... 200/61.45 R–61.45 M, 61.52; 73/61.41; 324/441, 446, 721, 724
    See application file for complete search history.

(56) References Cited

U.S. PATENT DOCUMENTS

| | | | | |
|---|---|---|---|---|
| 3,302,102 A | * | 1/1967 | Lace | G01N 27/07 324/149 |
| 3,488,461 A | * | 1/1970 | Nelson | 200/61.42 |
| 3,502,831 A | * | 3/1970 | McRoskey | 200/61.49 |
| 3,673,362 A | * | 6/1972 | Carlson et al. | 200/61.45 R |
| 3,748,899 A | * | 7/1973 | Gregg et al. | 73/170.34 |
| 3,771,457 A | * | 11/1973 | Buxton | F42C 19/06 102/262 |
| 4,331,923 A | * | 5/1982 | Akers, Jr. | G01R 27/22 324/442 |
| 4,608,468 A | * | 8/1986 | Bai | 200/61.45 R |
| 4,718,775 A | * | 1/1988 | Keznickl | 374/104 |

(Continued)

FOREIGN PATENT DOCUMENTS

KR     10-2002-0051647 A     6/2002

*Primary Examiner* — Michael A Lyons
*Assistant Examiner* — David L Singer
(74) *Attorney, Agent, or Firm* — Kaplan Breyer Schwarz & Ottesen, LLP (57) ABSTRACT

Provided is an internal switch-type salt meter in which an impact switching device operable by an impact applied into a main body is built in the main body so that it is unnecessary to separately waterproof the switching device. The salt meter includes a main body having the inside waterproofed against the outside, a sensor part disposed on an end of a side of the main body to detect salinity of an object to be measured, a display part disposed on a surface of a side of the main body to display a result measured by the sensor part, and a switching device built in the main body to generate a contact point by an impact with an external impact object, thereby operating the sensor part and the display part. The switching device may be built in the main body so that a separate waterproof process is not required.

2 Claims, 6 Drawing Sheets (56) References Cited

U.S. PATENT DOCUMENTS

| | | | | |
|---|---|---|---|---|
| 4,823,087 | A | * | 4/1989 | Sugimori ........................ 324/441 |
| 4,918,391 | A | * | 4/1990 | Byrd ........................ G01N 33/02 |
| | | | | 204/400 |
| 5,837,951 | A | * | 11/1998 | Kato et al. .............. 200/61.45 R |
| 5,955,712 | A | * | 9/1999 | Zakutin ........................ 200/61.48 |
| 6,545,235 | B1 | * | 4/2003 | Chou ........................... 200/61.51 |
| 6,949,713 | B2 | * | 9/2005 | Weng et al. ............ 200/61.45 R |
| 7,030,327 | B2 | * | 4/2006 | Matsumoto ............ 200/61.45 R |
| 8,367,952 | B2 | * | 2/2013 | Kelley, Jr. ............... 200/61.45 R |
| 2001/0007205 | A1 | * | 7/2001 | Urano ................... G01P 15/135 |
| | | | | 73/65.01 |
| 2011/0018725 | A1 | * | 1/2011 | Yang ........................ G01N 33/02 |
| | | | | 340/627 |
| 2011/0140704 | A1 | * | 6/2011 | Son ............................... 324/441 |

\* cited by examiner

AUTOMATIC SALT METER HAVING INTERNAL SWITCHING DEVICE

CROSS-REFERENCE TO RELATED APPLICATIONS

This application claims priority to Korean Patent Applications KR 10-2012-0013932 with a filing date of Feb. 10, 2012 and KR 10-2013-0000958 with a filing date of Jan. 4, 2013. Furthermore, aforementioned Korean Patent Applications KR 10-2012-0013932 and KR 10-2013-0000958 are incorporated herein by reference.

FIELD OF THE INVENTION

The present invention relates to a salt meter, and more particularly, to an internal switch-type salt meter in which an impact switching device operable by an impact applied into a main body is built in the main body so that it is unnecessary to separately waterproof the switching device.

BACKGROUND OF THE INVENTION

In general, salt meters measure salinity by using a property in which electrical conductivity is changed according to an ion concentration of sodium chloride (NaCl) contained in foods. That is, a pair of electrodes may contact an object to be measured (hereinafter, referred to as a measurement object), and then a voltage may be applied into the pair of electrodes to measure an amount of flowing current, thereby obtaining salinity of the corresponding object.

To measure salinity, a power button may be pushed in a state where a salt meter is put inside a cooking container to contact a food, or a measurement button may be pushed when the power button is turned on to measure the salinity of the food. That is, the salt meter should be immersed into a measurement object for a predetermined time, and also, a separate switch should be manipulated to measure the salinity. In addition, since a switch that is necessarily provided for manipulating is an electrical device, the switch must be waterproofed.

Figure 1:
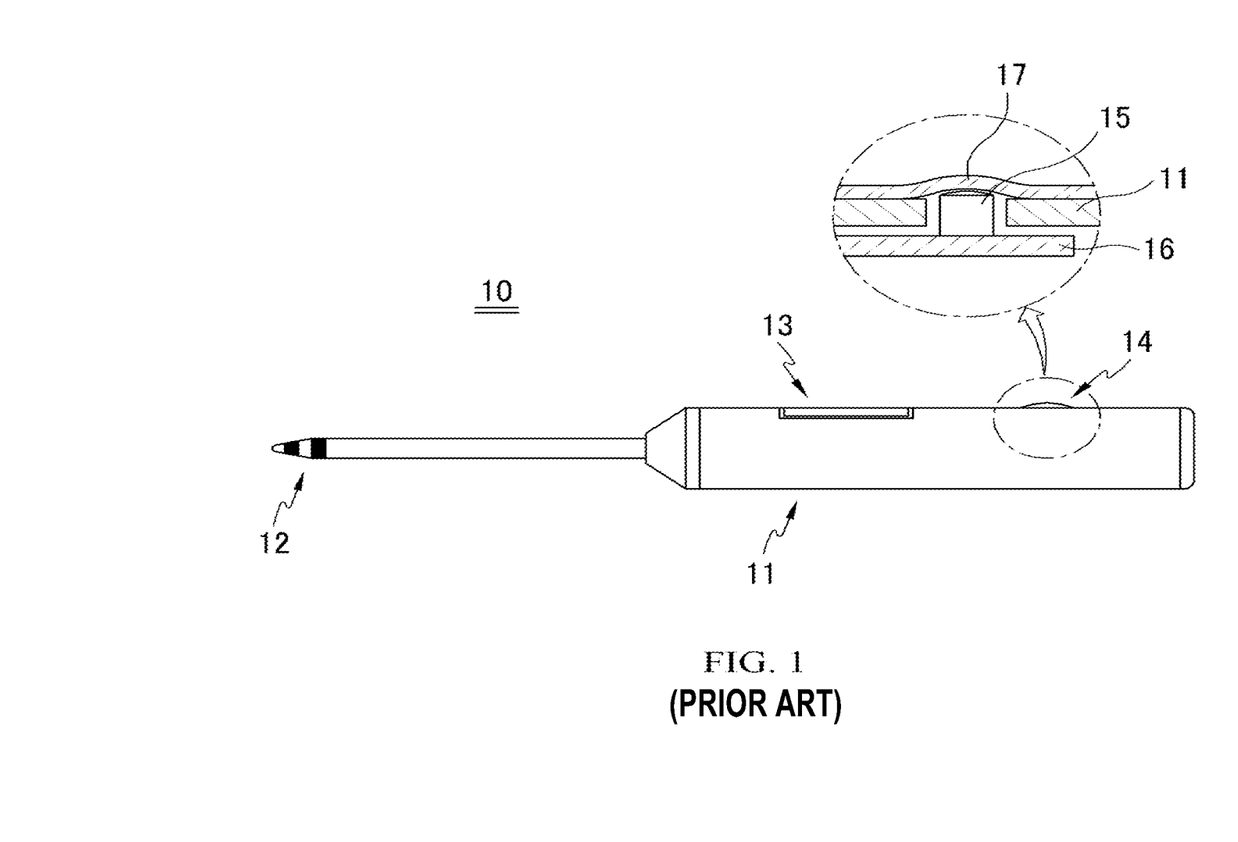
FIG. 1 is a perspective view of a salt meter according to a related art.

For this, a salt meter 10, as shown in FIG. 1, includes a measurement part 12, a display part 13, and a manipulation part 14 on a main body 11 defining an outer appearance thereof. The manipulation part 14 according to the related art includes a button type switch 15 which is generally exposed to the outside and is manipulated through a push or touch operation. The switch 15 is mounted on a board 16 on which a predetermined circuit is printed. The switch 15 has one side passing through a hole and exposed to the outside of the main body 11. Also, a waterproof film 17 surrounds the switch 11 together with the main body 11. Thus, the salt meter may measure salinity or temperature within the measurement object.

The switch operable by the push or touch operation as described above may be easily manipulated. However, as the switch is incalculably and repeatedly touched to wear the waterproof film 17. As a result, the switch is used for a long time to make a hole in the waterproof film, thereby losing the waterproof function. Also, when a measurement apparatus is manufactured, a process of attaching the separate waterproof film 17 for protecting the switch 15 should be performed. Thus, the manufacturing process may be complicated, and also, manufacturing costs may be increased. Also, to apply a switching device into the measurement apparatus being gradually miniaturized, the switching device should be gradually miniaturized. Thus, the push or touch operation by a user may be trouble to limit the miniaturization.

To solve the above-described limitations, a salt or temperature measurement apparatus which is operated by using electrical conductivity without a separate touch operation by the user is being proposed. However, since a basic power source should be continuously supplied into the measurement apparatus using the electrical conductivity to detect a flow of current between electrodes, it may be very disadvantageous in power consumption.

Currently, vibration detection apparatuses using elasticity are proposed with the purpose of earthquake sensing or security. However, such a vibration detection apparatus may detect only simple vibration and also not be used as a switching device for ON/OFF operation.

SUMMARY OF THE INVENTION

Accordingly, the present invention is directed to an automatic salt meter having internal switching device that substantially obviates one or more problems due to limitations and disadvantages of the related art.

An object of the present invention is to provide a temperature or salinity measurement apparatus in which a switching device is built in a main body so that a separate waterproof process is not required for the switching device to simplify a manufacturing process and reduce manufacturing costs.

Another object of the present invention is to provide a temperature or salinity measurement apparatus in which a separate power is not required for a switching operation to reduce power consumption, and which is operated by only an impact to prevent the measurement apparatus from malfunctioning by external vibration.

According to an aspect of the present invention, there is provided a salt meter including: a main body having the inside waterproofed against the outside; a sensor part disposed on an end of a side of the main body to detect salinity of an object to be measured; a display part disposed on a surface of a side of the main body to display a result measured by the sensor part; and a switching device built in the main body to generate a contact point by an impact with an external impact object, thereby operating the sensor part and the display part.

The switching device may include: a hollow housing; a coil extending inward from a side of the housing; and a support member supporting a side of the coil at a side of the housing, wherein an end of the coil electrically contacts the housing by elasticity of the coil due to the impact with the external impact object to cause a switching operation.

The housing may be formed of a conductive metal material. The housing may be partitioned into a plurality of regions in which the end of the coil electrically contacts the housing by an insulation member.

The switching device may further include a guide protrusion disposed on an inner wall between the plurality of partitioned regions of the housing.

The switching device may include: a hollow housing; a frame having a length greater than a diameter of the housing, the frame being coupled to the housing while being bent to cross an inner space of the housing; and a support member supporting both ends of the frame on both sides of the housing, wherein a central portion of the frame is changed in position according to an impact with an external impact object to electrically contact the housing, thereby causing a switching operation.

The housing may be electrically partitioned into both sides with respect to the frame by the insulation member.

DETAILED DESCRIPTION

Technical objectives of the present invention will become evident through the following embodiments. Hereinafter, exemplary embodiments of the present invention will be described in more detail with reference to the accompanying drawings.

Figure 2:
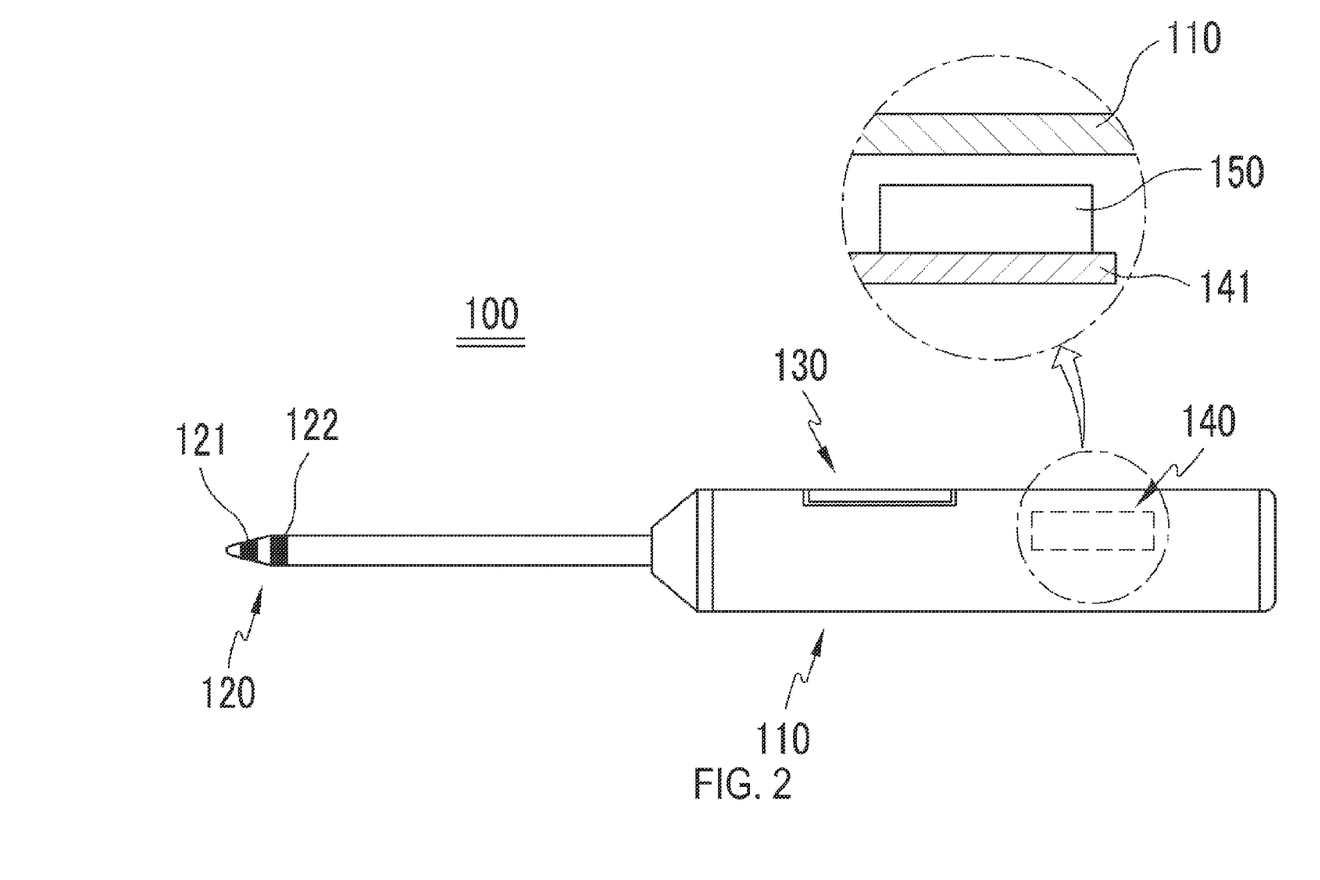
FIG. 2 is a perspective view of a salt meter according to an embodiment of the present invention.

FIG. 2 is a perspective view of a salt meter according to an embodiment of the present invention. Referring to FIG. 2, a salt meter 100 according to an embodiment of the present invention includes a main body 110 defining an outer appearance thereof, a measurement part 120 disposed on a side of the main body 110, a display part 130 disposed on a surface of a side of the main body 110, and a manipulation part 140 disposed within the main body 110.

Here, the main body 110 may be provided as an injection-molded container having a hollow therein and formed of a plastic material. Also, the main body 110 may have a bar shape on the whole to allow a user to easily grasp the salt meter 100. The main body 110 includes the measurement part 120, the display part 130, and the manipulation part 140. The salt meter 100 is typically used in a state where the salt meter 100 is immersed into a measurement object such as foods. Thus, the main body 110 may have structure with the inside and outside sealed.

The measurement part 120 is configured to measure salinity or temperature of the measurement object. The measurement part 120 is disposed on one end of the main body 110. The measurement part 120 typically includes a salinity detection sensor 121 for measuring salinity that is a concentration of NaCl contained in the measurement object. In recent, the measurement part 120 includes a temperature detection sensor 122 for measuring a temperature of the measurement object in addition to the salinity of the measurement object. The salinity detection sensor 121 includes a pair of sensor pins formed of plated bronze. The salinity detection sensor 121 measures the salinity by using a potential difference generated in each of the sensor pins.

The display part 130 displays an operation state of the salt meter 100 and the salinity and temperature detected by the measurement part 120.

The manipulation part 140 is a switching device for manipulating an operation of the salt meter 100 such as an ON/OFF operation of the salt meter 100 or a measurement mode change of the salinity and temperature. As shown in FIG. 2, the manipulation part 140 is disposed within the main body 110. The manipulation part 140 is mounted on a typical board 141. Also, the manipulation part 140 is electrically connected to a circuit printed on the board 141 to transmit a switching signal into a control part (not shown) built in an IC chip shape. Here, the main body 110 may be sealed again the outside and completely waterproofed to prevent internal parts from electrically malfunctioning. Particularly, the manipulation part 140 according to an embodiment of the present invention may be switched in a state where the manipulation part 140 is disconnected to the outside. That is, the manipulation part 140 may be switched by an impact of the main body itself, but not by an external push or touch operation. Hereinafter, the manipulation part 140 will be described in detail.

Figure 3:
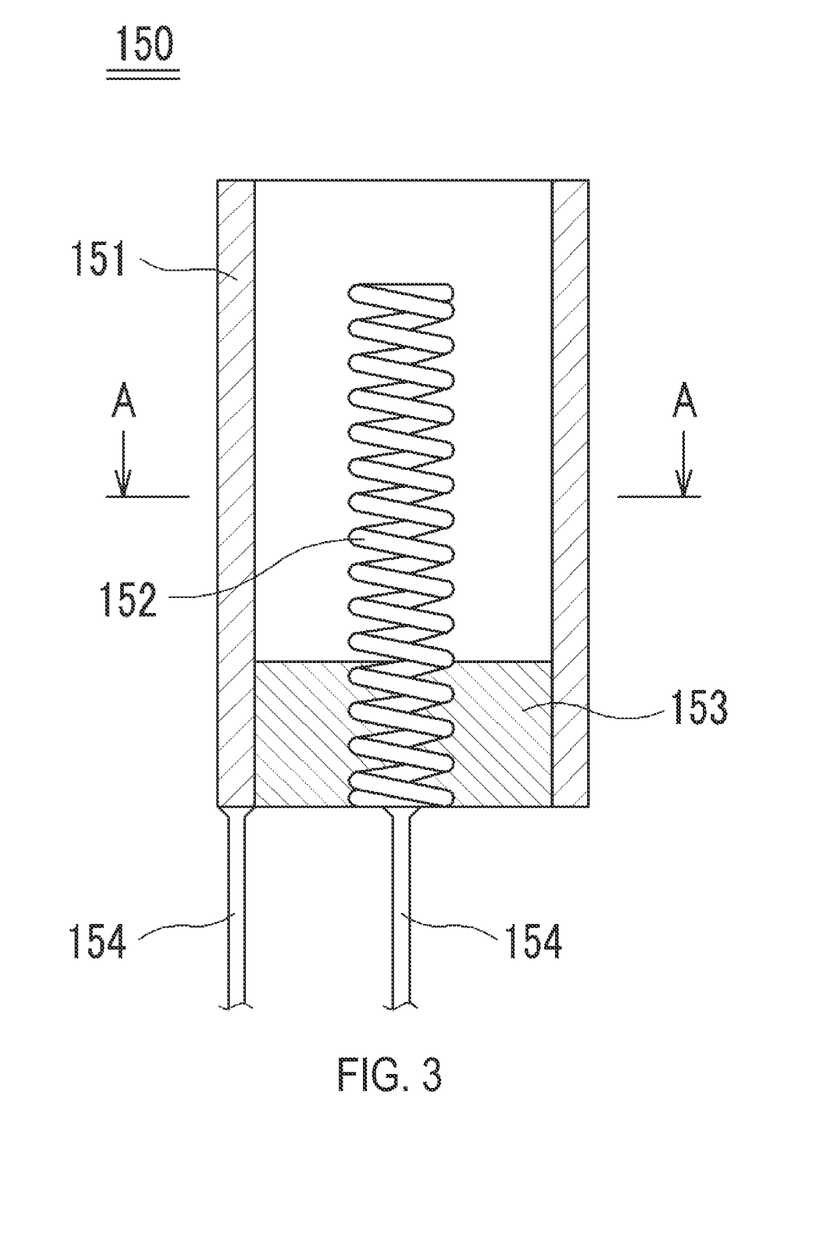
FIG. 3 is a cross-sectional view illustrating a schematic structure of a switching device according to an embodiment of the present invention.

FIG. 3 is a cross-sectional view illustrating a schematic structure of a switching device according to an embodiment of the present invention. A switching device 150 according to an embodiment of the present invention includes an impact switch using elasticity of a coil.

In detail, the switching device 150 includes a housing 151, an elastic coil 152 disposed within the housing 151, a support member 153 supporting the elastic coil 152 within the housing 151, and a wire 154 connected to each of sides of the housing 151 and the elastic coil 152.

Here, the housing 151 defines an outer appearance of the switching device 150. The housing 151 has a hollow circular shape or a polygonal cylindrical shape. The hollow housing 151 receives the coil 152 and the support member 153 therein. The housing 151 may be formed of an electrical nonconductor such as plastic for insulating. In this case, a separate electrode should be provided. According to the present invention, the housing 151 is formed of an electrical conductor so that the housing itself serves as an electrode. For example, the housing 151 according to the present invention may be formed of bronze.

The coil 152 has an end which is changed in position by an impact. Thus, the coil 152 may be configured to perform a switching operation. The coil 152 has one end fixed to the housing 151 by the support member 153 and the other end disposed in an inner space of the housing 151. Here, the other end of the coil 152 is disposed at a central portion with respect to an inner wall of the housing 151. Particularly, the coil 152 according to the present invention may include coil having an elastic modulus and sufficient hardness which is not deformed by external vibration. The coil 152 may be formed of an electrical conductor such as phosphor bronze to apply an electrical signal.

The support member 153 supports one end of the coil 152 on a side of the housing 151. The support member 153 may be formed of plastic that is an electrical nonconductor or an injection-molded resin material to electrically insulate the housing 151 from the coil 152.

The switching device 150 is built in the main body 110 of the salt meter 100 to perform a switching operation even as the salt meter 100 is impacted into an external impact object.

Figure 4:
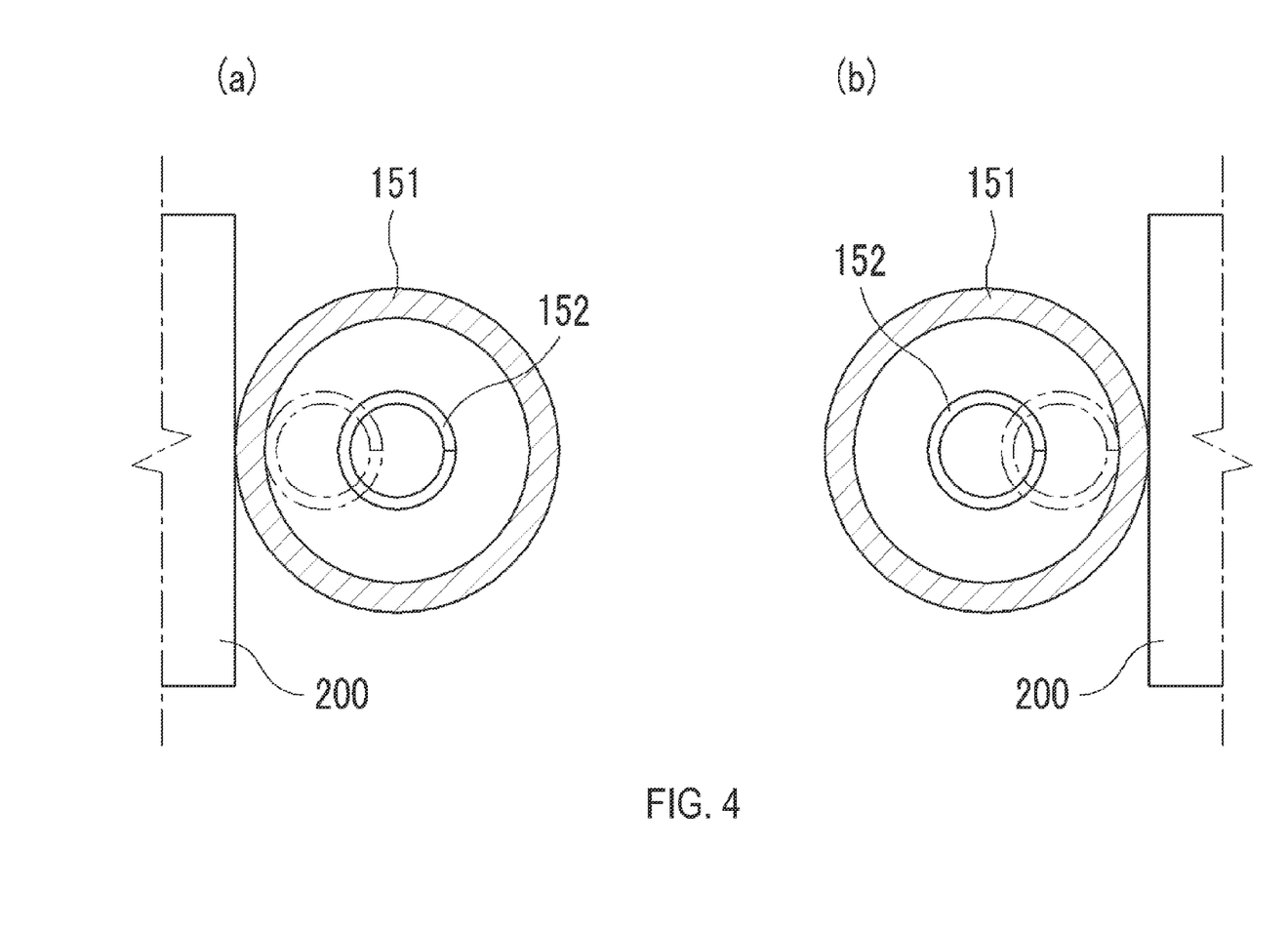
FIG. 4 is a cross-sectional view illustrating various switching operations in the switching device of FIG. 3.
Figure 5:
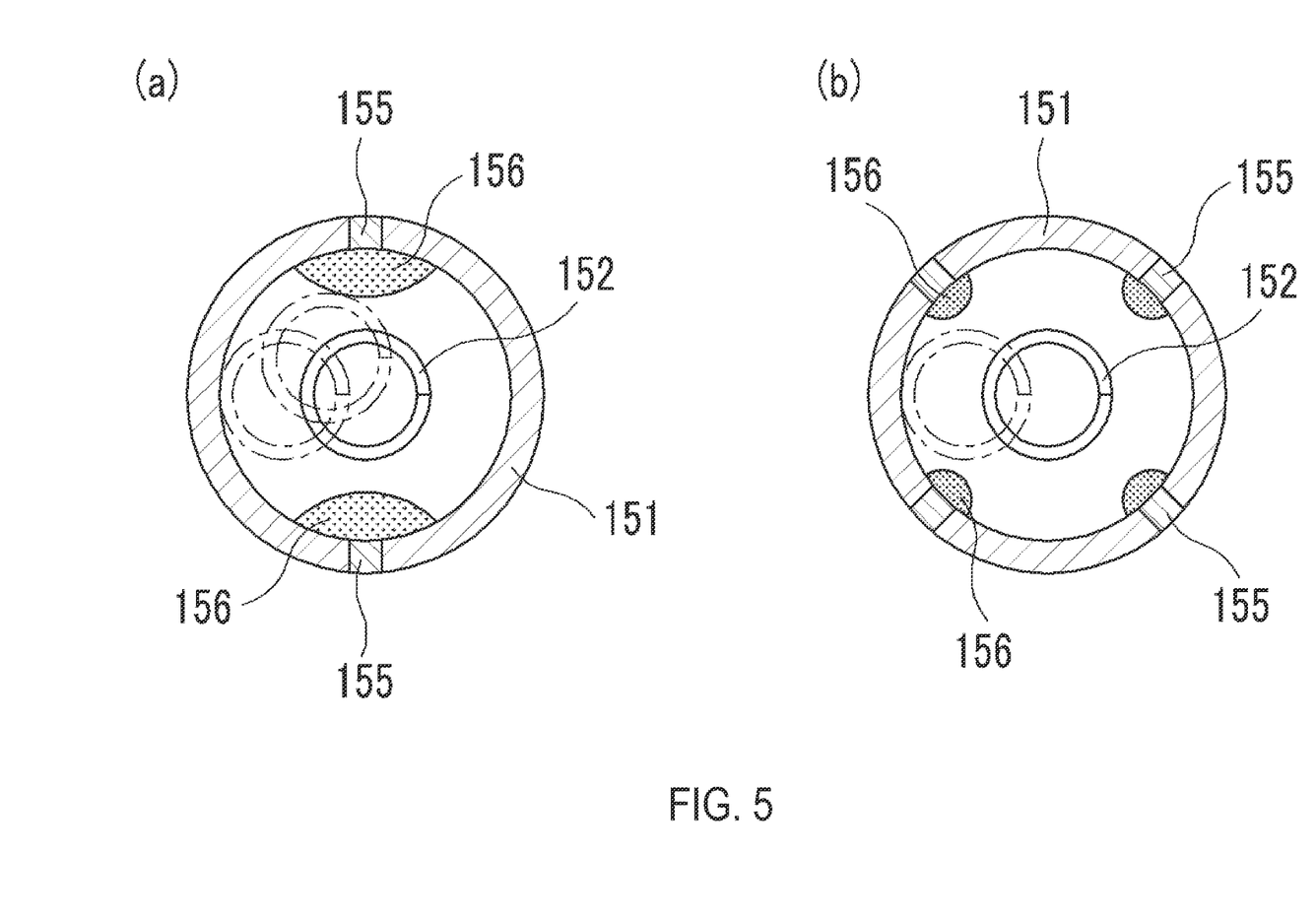
FIG. 5 is a cross-sectional view illustrating a modified example of the switching device of FIG. 3.

FIG. 4 is a cross-sectional view illustrating various switching operations in the switching device of FIG. 3. FIG. 5 is a cross-sectional view illustrating a modified example of the switching device of FIG. 3. FIGS. 4 and 5 illustrate cross-sections in an A-A direction, respectively.

A switching operation of the switching device 150 according to an embodiment of the present invention will be described with reference to FIG. 4. Referring to FIG. 4A, when the switching device 150 is impacted onto an impact object 200 while being moved in a left direction, an end of the coil 152 may be instantaneously changed in position in a direction of the impact object 200 by impact inertia to return to its original position. Here, the end of the coil 152 and a left inner wall of the housing 151 may instantaneously contact each other to cause a switching operation. Similarly, referring to FIG. 4B, when the switching device 150 is impacted onto an impact object 200 while being moved in a right direction, an end of the coil 152 may be instantaneously changed in position in a direction of the impact object 200 by impact inertia to return to its original position. Here, the end of the coil 152 and a right inner wall of the housing 151 may instantaneously contact each other to cause a switching operation. Due to the instantaneous position change of the coil 152, the housing 151 and the coil 152 may contact each other to cause an electrical switching operation.

Here, the coil 152 may have an elastic modulus with sufficient intensity which is not shaken by external vibration. In general, the impact inertia may have greater by about 5 times to about 7 times than vibration inertia. Also, an impact amount may be proportional to the product of an acting force and a time. Thus, even though the coil 152 is designed so that the coil 152 is not shaken by the external vibration, since a strong inertial force instantaneously occurs by the impact, the end of the coil 152 may be sufficiently changed in position by the inertia. Also, although the switching device 150 is directly impacted onto the impact object 200 in the description of the switching operation, since the switching device 150 is disposed within the main body of the salt meter 100, the salt meter 100 is impacted onto the impact object 200 to cause the same switching operation. Also, a user's hand may be used as the impact object 200.

Referring to FIG. 5, in the switching device 150 according to an embodiment of the present invention, the housing 151 is partitioned into a plurality of regions. Also, a guide protrusion 156 may be further disposed on the inner wall of the housing 151.

According to the present invention, the housing 151 may be formed of bronze so that the housing itself 151 serves as the electrode. Here, the housing (the electrode) 151 may be partitioned into two regions as shown in FIG. 5A or four regions as shown in FIG. 5B by the insulation member 155. When the housing 151 is integrally manufactured, the switching device 150 may perform only an ON/OFF operation. However, when the housing 151 is partitioned in the two regions as shown in FIG. 5A, the two regions may be classified into control signals such as an "increase (+)" and a "decrease (−)". Also, when the housing 151 is partitioned into the four regions as shown in FIG. 5B, the four regions may be classified into various control signals such as an "increase (+), a "decrease (−)", a "left movement", and a 'right movement". The number of regions of the housing 151 partitioned into a plurality of regions may be variously set according to the purpose of use. Here, the wire 154 may be connected to the coil 152 and an end of a side of each housing 151 and thus be electrically connected to the board 141. Also, the wire 154 may be connected to a control part and a power source part through the circuit printed on the board 141.

Also, the guide protrusion 156 may be disposed inside the insulation member 155, i.e., on an inner wall between the plurality of regions of the housing 151. Thus, even if the switching device 150 is exactingly impacted in a specific direction, the end of the coil 152 may be impacted onto a specific region of the housing 151. That is, since it is difficult to impact the switching device, i.e., the salt meter 100 in an accurate direction, even if the impact direction is somewhat out of a target position, the end of the coil 152 may be guided into the regions of the housing 151 by the guide protrusion 156 in a direction to be impacted. The guide protrusion 156 may have a spherical or aspheric shape and be formed of an insulation material.

Figure 6:
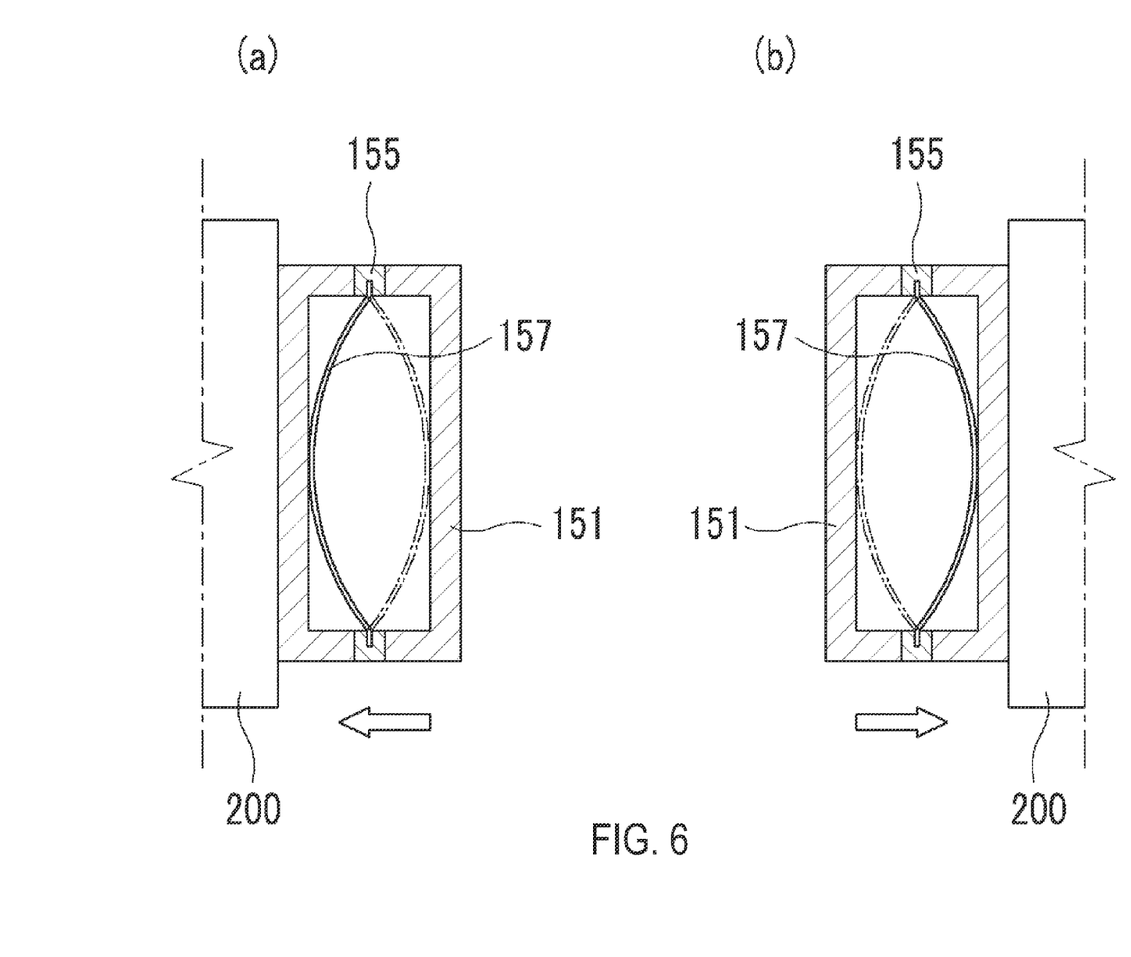
FIG. 6 is a cross-sectional view illustrating a switching operation in a switching device according to another embodiment of the present invention.

FIG. 6 is a cross-sectional view illustrating a switching operation in a switching device according to another embodiment of the present invention. A switching device 150 according to another embodiment of the present invention includes an impact switch using elasticity of a frame 151.

Referring to FIG. 6, the switching device 150 according to another embodiment of the present invention includes a housing 151 and a frame 157 coupled to the housing 151 while crossing an inner space of the housing 151. The housing 151 may be formed of bronze to serve as an electrode. The frame 157 may be fixed to the inside of the housing 151 by an insulation member 155 to insulate the housing 151 from the frame 157. The insulation member 155 may support the frame 157, and also partition the inside of the housing 151 into both regions with respect to the frame 157 so that the housing 151 includes two electrodes.

In the switching device 151 according to another embodiment of the present invention, the housing 151 may have a rectangular shape in section. Also, the frame 157 having a predetermined width and thickness may bisectionally cross the inner space of the housing 151 along a long direction of the housing 151. Here, the frame 157 may have a length greater than that in the long direction of the inner space of the housing 151. Also, the frame 157 may be bent as shown in FIG. 6. Here, a central portion of the bent frame 157 may contact an inner wall of the housing 151 in a short direction of the inner space.

Referring to the switching operation of the switching device 150 according to another embodiment of the present invention, as shown in FIG. 6A, when the switching device 150 is impacted into an impact object 200 while being moved in a left direction, the central portion of the frame 157 may be changed in contact position on a left inner wall of the housing 151 in a direction of the impact object 200 by impact inertia. Also, in this state, as shown in FIG. 6B, when the switching device 150 is impacted onto the impact object 200 while being moved in a right direction, the central portion of the frame 157 may be changed in contact position on a right inner wall of the housing 151. When the above-described processes are repeatedly performed, the frame 157 may perform the switching operation with respect to a left electrode 154 and a right electrode 154.

As described above, the manipulation part according to the embodiments of the present invention may perform the switching operation by simply impacting the main body of the salt meter onto the object such as a palm. Also, the salt meter may be turned on or off through the sample impact operation to reduce power consumption. Also, although the switching device using the impact is applied into the salt meter in the description of the present invention, the switching device may be applied into various measurement devices such as a thermometer in addition to the salt meter. That is, the salt meter according to the present invention may include various measurement devices such as the thermometer.

According to the present invention, the switching device may be built in the main body so that a separate waterproof process is not required for the switching device to simplify the manufacturing process and reduce the manufacturing costs.

Also, according to the present invention, a separate power may not be required for the switching operation to reduce power consumption, and the salt meter may be operated by only the impact to prevent the salt meter from malfunctioning by the external vibration.

Also, the ON/OFF operation due to the impact may be applied into the switching device using the impact.

It will be apparent to those skilled in the art that various modifications and variations can be made in the present invention. Thus, it is intended that the present invention covers the modifications and variations of this invention provided they come within the scope of the appended claims and their equivalents.

What is claimed is:

1. A salt meter comprising:
   a main body having the inside waterproofed against the outside;
   a sensor part disposed on an end of a side of the main body to detect salinity of an object to be measured;
   a display part disposed on a surface of a side of the main body to display a result measured by the sensor part; and
   a switching device built within the main body to generate a contact point, wherein the contact point is generated by impacting the main body against an object that is external to the main body, thereby operating the sensor part and the display part,
   wherein the switching device comprises:
   (i) a hollow housing electrically partitioned into a plurality of regions by an insulation member, with each partitioned region outputting a different control signal,
   (ii) a coil extending inward from a side of the housing,
   (iii) a support member supporting a side of the coil at a side of the housing, the support member being formed from an electrical nonconductor material, and
   (iv) a guide protrusion disposed on an inner wall between the plurality of regions of the housing to guide an end of the coil in an impacted direction of the main body, the guide protrusion being formed from an electrical insulation material, and
   wherein an end of the coil is adapted to electrically contact the plurality of regions as a result of:
   (i) an elastic characteristic of the coil, and
   (ii) the external impact of the main body against the object,
   thereby causing a control signal associated with the contacted region to be outputted to a circuit for performing a switching operation of the salt meter.

2. The salt meter of claim 1, wherein the housing is formed of a conductive metal material.

* * * * *